US008809274B2

(12) United States Patent
Suh (10) Patent No.: US 8,809,274 B2
(45) Date of Patent: *Aug. 19, 2014

(54) ADHESIVE HEMOSTATIC AGENT BASED ON PORCINE ATELOCOLLAGEN AND METHOD FOR PRODUCTION THEREOF

(75) Inventor: Hwal Suh, Seoul (KR)

(73) Assignees: Dalim Biotech Co., Ltd., Kyeonggi (KR); Industry-Academic Cooperation Foundation, Yongsei-University, Seoul (KR)

( * ) Notice: Subject to any disclaimer, the term of this patent is extended or adjusted under 35 U.S.C. 154(b) by 203 days.

This patent is subject to a terminal disclaimer.

(21) Appl. No.: 13/238,343

(22) Filed: Sep. 21, 2011

(65) Prior Publication Data

US 2012/0010143 A1    Jan. 12, 2012

Related U.S. Application Data

(63) Continuation-in-part of application No. 12/423,965, filed on Apr. 15, 2009, now Pat. No. 8,067,374.

(30) Foreign Application Priority Data

Apr. 16, 2008    (KR) .......................... 10-2008-0034957

(51) Int. Cl.
| | | |
|---|---|---|
| *A61K 38/36* | (2006.01) | |
| *A61P 7/04* | (2006.01) | |
| *A61K 33/42* | (2006.01) | |
| *A61K 33/14* | (2006.01) | |
| *A61L 24/10* | (2006.01) | |
| *A61K 38/39* | (2006.01) | |
| *A61K 31/198* | (2006.01) | |

(52) U.S. Cl.
CPC .................. *A61K 33/14* (2013.01); *A61K 33/42* (2013.01); *A61L 24/102* (2013.01); *A61K 38/39* (2013.01); *A61K 31/198* (2013.01); *A61L 2400/04* (2013.01)
USPC .......................... 514/17.2; 530/356; 530/410

(58) Field of Classification Search
USPC ................................................ 530/356, 410
See application file for complete search history.

(56) References Cited

U.S. PATENT DOCUMENTS

| 4,215,200 | A | * | 7/1980 | Miyata et al. ................. 435/273 |
|---|---|---|---|---|
| 4,271,070 | A | | 6/1981 | Miyata et al. |
| 4,559,304 | A | | 12/1985 | Kasai et al. |
| 5,219,895 | A | | 6/1993 | Kelman et al. |
| 5,332,802 | A | | 7/1994 | Kelman et al. |
| 5,464,471 | A | | 11/1995 | Whalen et al. |
| 5,605,887 | A | | 2/1997 | Pines et al. |
| 5,773,033 | A | | 6/1998 | Cochrum et al. |
| 5,883,078 | A | | 3/1999 | Seelich et al. |
| 2008/0181936 | A1 | * | 7/2008 | Filatov et al. ................. 424/445 |

FOREIGN PATENT DOCUMENTS

| EP | 0569551 B1 | 10/2002 |
|---|---|---|
| WO | 9800180 A1 | 1/1998 |

OTHER PUBLICATIONS

Gade et al. ("The stabilization of fibrillar collagen matrices with 3,4-dihydroxyphenylalanine," J. Biomedical Materials Research, 2004, vol. 25, pp. 799-811).*
Gabe et al. ("The stabilization of fibrillar collagen matrices with 3,4-dihydroxyphenylalanine," J. Biomedical Materials Research, 2004, vol. 25, pp. 799-811).*
Fraenkel-Conrat et al., Esterification of Proteins with Alcohols of Low Molecular Weight, Journal of Biological Chemistry, 1945, vol. 161, pp. 259-268.
Vakos et al., In Vacuo Esterification of Carboxyl Groups in Lyophilized Proteins, Journal of Protein Chemistry. 2001; vol. 20, No. 6; pp. 521-531.

* cited by examiner

*Primary Examiner* — James H Alstrum Acevedo
*Assistant Examiner* — Tara Martinez
(74) *Attorney, Agent, or Firm* — Egbert Law Offices, PLLC (57) ABSTRACT

Disclosed is an adhesive hemostatic agent based on non-blood constituents including DOPA, able to strongly adhere to collagen fibers, and which comprises an antifibrinolytic agent in addition to an esterified atelocollagen which is non-immunogenic and may become positively charged thereon such that the adhesive hemostatic agent has no possibility of mediating particular diseases or viral infections (HIV, HCV, HBV, CMV, etc), unlike conventional agents comprising blood constituents, and readily binds to negatively charged platelets at high adhesive strength, thus inducing quick blood coagulation. Also, provided is a method for preparing the same.

3 Claims, 7 Drawing Sheets

ADHESIVE HEMOSTATIC AGENT BASED ON PORCINE ATELOCOLLAGEN AND METHOD FOR PRODUCTION THEREOF

CROSS-REFERENCE TO RELATED U.S. APPLICATIONS

The present application is a continuation-in-part of U.S. patent application Ser. No. 12/423,965, filed on Apr. 15, 2009, and entitled "Adhesive Hemostatic Agent Based on Porcine Atelocollagen and Method for Production Thereof", presently pending.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to an adhesive hemostatic agent free of blood constituents, which is useful in surgical operations, and a method for the production thereof.

Porcine collagen is used as an active ingredient of the adhesive hemostatic agent. In order to be used, porcine collagen is rendered non-immunogenic by removing telopeptides therefrom. The resulting atelocollagen is esterified to give positive charges thereon, which enable the collagen to bind faster to negatively charged platelets, thus eliciting haemostasis quickly. In addition, 3,4-dihydroxy-phenyl alanine (hereinafter referred to as "DOPA"), highly adhesive to plasma proteins, when in a salt solution, can ensure high adhesive strength and blood coagulation activity for the collagen-based adhesive hemostatic agent. Further, an antifibrinolytic may be added in a trace amount to the collagen-based adhesive hemostatic agent.

Based on the fact that blood coagulation starts when platelets bind to collagen, the ubiquitous extracellular matrix, the present invention contemplates a collagen-based adhesive hemostatic agent greatly improved in anti-hemorrhage and tissue sealing activity and a method for preparing the same. Instead of bovine collagen, porcine collagen, free of TSE's (Transmissible Spongiform Encephalopathies), is made non-immunogenic by the removal of telopeptides therefrom, and the carboxylic acid groups of the non-immunogenic collagen are esterified with ethanol such that the atelocollagen is positively charged and thus can bind quickly to negatively charged platelets, inducing haemostasis quickly. In addition, the use of DOPA (3,4-dihydroxy-phenyl alanine), functioning to stabilize collagen fibers, in combination with salt and an antifibrinolytic ensures excellent adhesive strength and tissue sealing activity for the collagen-based adhesive hemostatic agent.

2. Description of Related Art Including Information Disclosed Under 37 CFR 1.97 and 37 CFR 1.98

Haemostatis and tissue gluing are very important in surgical operations because they lead to fast post-operative healing of wounds and tissue sealing. Like 'Beriplast P' (Aventis)™, 'Greenplast kit' (Green Cross)™, 'Tisseel kit' (Baxter AG)™, 'Tissucol Duo Quick' (Baxter AG)™, 'TachoSil' (Nycomed)™ and 'Tachocomb' (Nycomed)™, most conventional haemostatic bio-glues or bio-adhesives employ blood constituents such as fibrinogen, thrombin, etc., and thus are based on the blood coagulation process in which thromboplastin, together with calcium, activates prothrombin to thrombin, which in turn converts fibrinogen into fibrin which is cross-linked in the presence of transglutaminase (Factor XIII) to form fibrin clots. Because the basic materials of the conventional haematostatic bio-glues or bio-adhesives are derived from blood constituents and have the possibility of being infected with viruses such as HIV, HBV, HCV and CMV, strict regulations are imposed on the preparation of the haemostatic bio-glues or bio-adhesives as well as the securing and storing of the basic materials.

Particularly, the haematostatic products 'Greenplast kit'™, 'Tisseel kit'™, 'Tissucol Duo Quick'™, and 'Tachocomb'™ additionally contain aprotinin, a protein isolated from bovine lung, as an antifibrinolytic, but cause anaphylaxis or a severe allergic reaction though at a very low rate.

Recently, hemostatic agents based on non-blood constituents have been developed and are commercially available, like 'Avitene' (Alcon)™ and 'Helitene' (Duhamed)™. However, having single collagen components, they are very expensive and are used for hemostatic agent only due to their lacking a tissue gluing activity.

Other hemostatic agents can be found in U.S. Pat. No. 5,464,471 entitled "Fibrin Monomer Based Tissue Adhesive", 1995, U.S. Pat. No. 5,883,078 entitled "Hemostatic and Tissue Adhesive", 1999, U.S. Pat. No. 5,773,033, entitled Fibrinogen/chitosan hemostatic agents", 1998, U.S. Pat. No. 5,605,887 entitled "Therapeutic Fibrinogen Compositions", 1997. Likewise, these agents employ blood constituents including fibrinogen, thrombin, coagulants, aprotinin, bovine proteins and the like, thus raising concerns about contamination with particular pathogens and excessive costs for securing and storing materials and preparing the products. Conventional non-blood hemostatic agents employing collagen show anti-hemorrhage effects only, but do not function as tissue adhesives.

BRIEF SUMMARY OF THE INVENTION

It is an object of the present invention to provide an esterified collagen-based adhesive hemostatic agent which is free of blood constituents and effective in wound-healing hemostasis and tissue sealing, and a method for the preparation thereof.

It is another object of the present invention to provide an adhesive hemostatic agent based on non-blood constituents including DOPA, able to strongly adhere to collagen fibers, and which comprises an antifibrinolytic agent in addition to an esterified atelocollagen which is non-immunogenic and may become positively charged thereon such that the adhesive hemostatic agent has no possibility of mediating particular diseases or viral infections (HIV, HCV, HBV, CMV, etc), unlike conventional agents comprising blood constituents, and readily binds to negatively charged platelets at high adhesive strength, thus inducing quick blood coagulation.

The above objects could be accomplished by a provision of an adhesive hemostatic agent based on non-blood constituents, which comprises porcine esterified atelocollagen, which is free of TSE's (Transmissible Spongiform Encephalopathies) unlike bovine proteins, causes no immune responses and can become positively charged thereon allowing for quick binding to negatively charged platelets, L-DOPA (3,4-dihydroxy-phenyl alanine) which functions to stabilize collagen fibers, thus increasing the adhesive activity of the adhesive hemostatic agent, and a salt which serves to promote coagulation.

BRIEF DESCRIPTION OF THE SEVERAL VIEWS OF THE DRAWINGS

The above and other objects, features and other advantages of the present invention will be more clearly understood from the following detailed description taken in conjunction with the accompanying drawings.

DETAILED DESCRIPTION OF THE INVENTION

In accordance with an aspect thereof, the present invention pertains to an adhesive hemostatic agent. Unlike conventional hemostatic agent employing blood constituents, the adhesive hemostatic agent is based on esterified atelocollagen prepared from porcine collagen via telopeptide removal and esterification, keeping in mind the fact that collagen interacts with platelets in the blood coagulation process.

The adhesive hemostatic agent according to the present invention may comprise further functional ingredients for promoting coagulation and/or improving tissue sealing, such as clotting promoters, sealing improvers, and antifibrinolytics, in addition to the esterified atelocollagen from pigs.

In accordance with another aspect thereof, the present invention pertains to a method for preparing a porcine collagen-based adhesive hemostatic agent. The method comprises removing immunogenic telo-peptides from porcine collagen through enzyme (pepsin) treatment to afford atelocollagen, and reacting an aqueous 0.5~5 wt % solution of atelocollagen with a 65~95 wt % ethanol solution at 4° C. for 24~48 hrs with stirring, following by adjusting a pH of the solution to 7.4 with 0.1~1 M acetic acid to produce esterified collagen-based adhesive hemostatic agent.

The esterification of atelocollagen for use in the esterified collagen-based adhesive hemostatic agent of the present invention is illustrated as follows.

Esterification

Native collagens from pigs cause immune responses due to the telo-peptides attached on both ends thereof. Thus, the removal of the immunogenic telo-peptides results in atelocollagens which can be safely used without eliciting immune responses. Additionally, atelocollagen is subjected to esterification with ethanol to give esterified atelocollagen which is positively charged at pH 7.4 and can bind negatively charged platelets fast and easily.

The esterified atelocollagen according to the present invention is examined for blood coagulation potential in terms of the time taken to cause blood clots. For reference, atelocollagen and anionic succinylated atelocollagen are used. No clots were formed when succinylated atelocollagen was added, and atelocollagen was observed to form blood clots in 4~5 min whereas it took only 2~3 min for the esterified atelocollagen to form blood clots. Thus, the esterified atelocollagen rapidly binds to platelets, showing superior blood coagulation potential over atelocollagen or succinylated atelocollagen.

In accordance with an embodiment of the present invention, the adhesive hemostatic agent of the present invention, in addition to the esterified atelocollagen, comprises a functional material for improving adhesiveness, promoting blood clotting, increasing lysis and/or inhibiting fibrinolysis.

For example, 30~70 wt % of a solution of 0.5~5 wt % esterified atelocollagen in water is mixed with 30~70 wt % of a solution of 0.1~1 wt % DOPA (3,4-dihydroxy-phenyl alanine) in water with stirring at 4° C. to give a collagen-based adhesive hemostatic agent which is improved in adhesiveness.

In addition, an aqueous salt solution may provide an additional adhesive potential for the collagen-based adhesive hemostatic agent. In this regard, 30~70 wt % of a solution containing esterified atelocollagen in an amount of 0.5~5 wt % is mixed with 30~70 wt % of an aqueous solution containing DOPA (3,4-dihydroxy-phenyl alanine) in an amount of 0.1~1 wt % and a salt in an amount of 0.5~5 wt % with stirring at 4° C. Functioning to increase the solubility of DOPA, the salt may be selected from a group consisting of calcium chloride, sodium chloride, calcium chlorophosphate, and sodium chlorophosphate.

In an alternative embodiment, 30~70 wt % of a solution containing esterified atelocollagen in an amount of 0.5~5 wt % is mixed with 30~70 wt % of an aqueous solution containing DOPA in an amount of 0.1~1 wt %, a salt in an amount of 0.5~5 wt % and a collagen fibrinolysis inhibitor in an amount of 0.001~0.1 wt % with stirring at 4° C. to afford a collagen-based adhesive hemostatic agent preventive of collagen fibrinolysis. Also, even an aqueous solution containing an antifibrinolytic in an amount of 0.001~0.1 wt % alone can impart the function of inhibiting collagen fibrinolysis to the esterified collagen-based adhesive hemostatic agent.

Useful as a collagen fibrinolysis inhibitor in the present invention is tranexamic acid or aminocaproic acid.

Caution must be exercised to conduct the stirring at 4° C. because a higher temperature is likely to degenerate the collagen while a lower temperature decreases the solubility of collagen.

DOPA, serving as a functional ingredient in the esterified collagen-based adhesive hemostatic agent of the present invention, is oxidized into catecholamine which is in turn associated with a lysine moiety of the collagen, accounting for the strong adhesiveness of the adhesive hemostatic agent. Also, DOPA can stabilize collagen fibers. The salt improves the solubility of DOPA, thus further increasing the adhesiveness. Examples of the salt useful in the present invention include calcium chloride, sodium chloride, calcium chlorophosphate and sodium chlorophosphate, with preference to calcium chloride. Inhibiting the activity of plasminogen, tanexamic acid or aminocaproic acid ((4-aminomethyl)cyclohexan-1-carboxylicacid) are useful as an antifibrinolytic in the present invention.

Additional functions and effects of the ingredients used in the collagen-based adhesive hemostatic agent of the present invention are further delineated in the following examples.

A better understanding of the present invention may be obtained through the following examples which are set forth to illustrate, but are not to be construed as limiting the present invention.

EXAMPLE 1

Preparation of Esterified Atelocollagen with Ethanol

1. Native porcine collagen was treated with an enzyme (pepsin) to remove telopeptides, an immunogen, from both ends thereof, resulting in atelocollagen.
2. The atelocollagen was added in an amount of 2 wt % to a 75 wt % ethanol solution, followed by vigorous stirring at 4° C. for 24~48 hours.
3. The pH of the solution was adjusted to 7.4 with 0.5 M acetic acid.

As a result, an esterified atelocollagen was obtained, and it could be solely used to prepare an adhesive hemostatic agent.

Esterification was confirmed by FT-IR and MALDI-TOF. There was a spectral difference between atelocollagen and esterified atelocollagen.

Figure 1A:
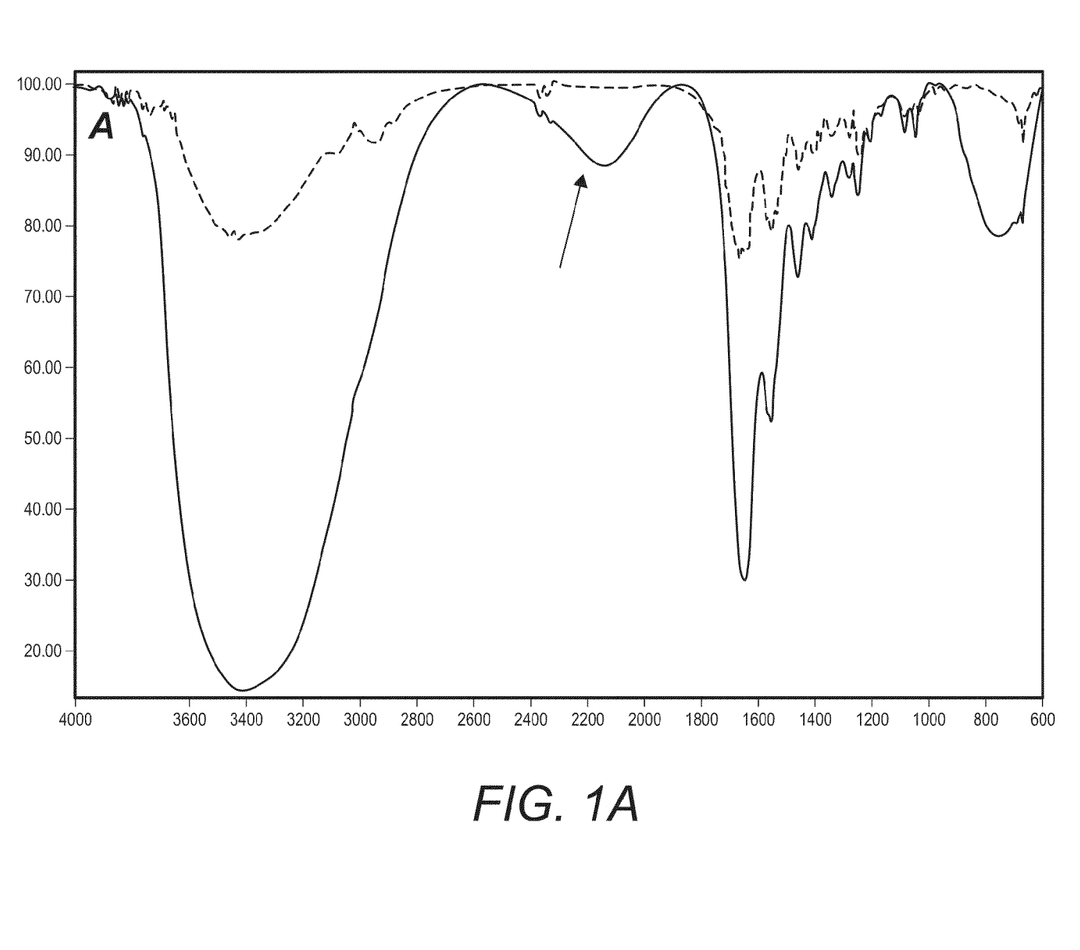
FIG. 1a is an FT-IR spectra of atelocollagen (emerald color) and esterified atelocollagen (brown).
Figure 1B:
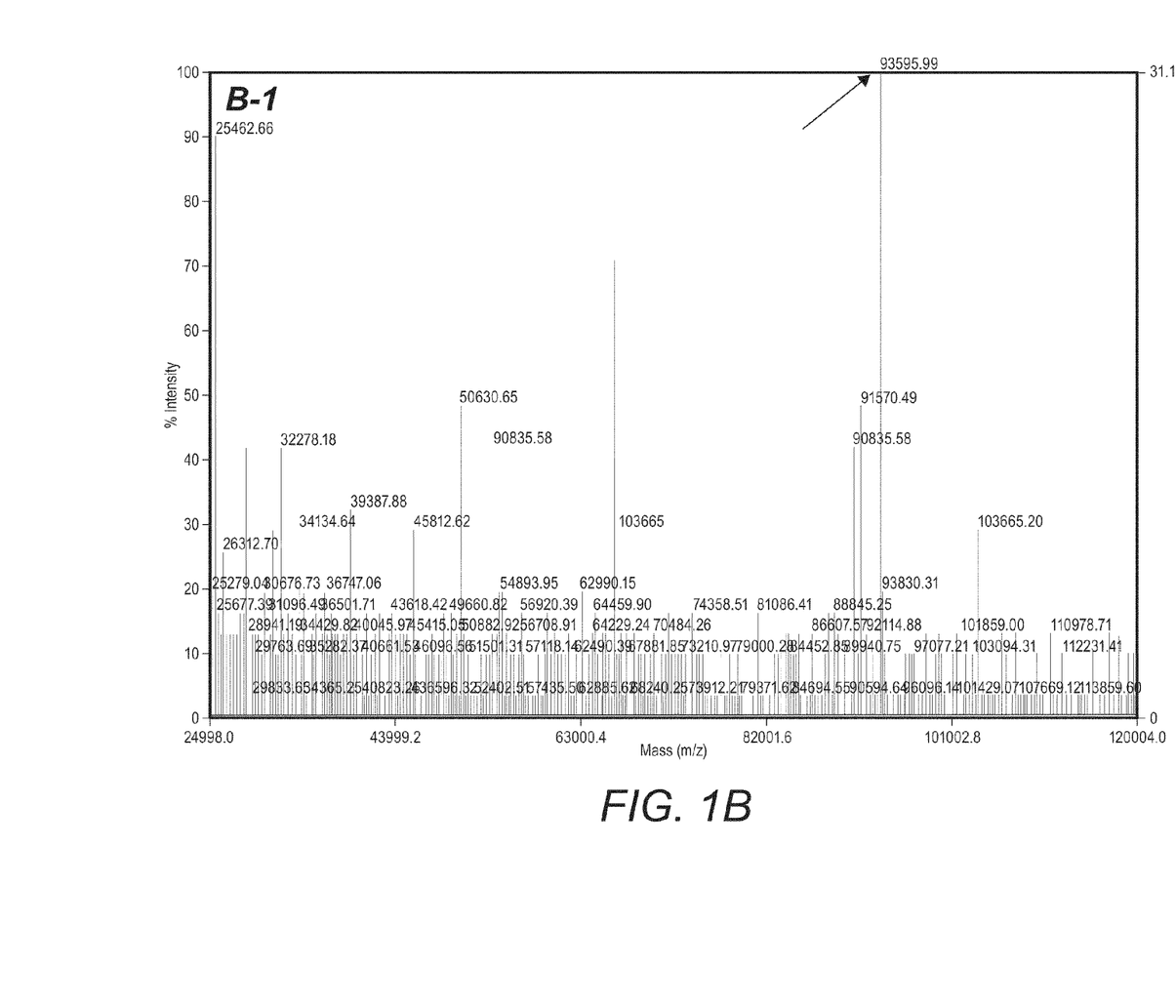
FIG. 1b is a MALDI-TOF spectrum of atelocollagen (B-1).
Figure 1C:
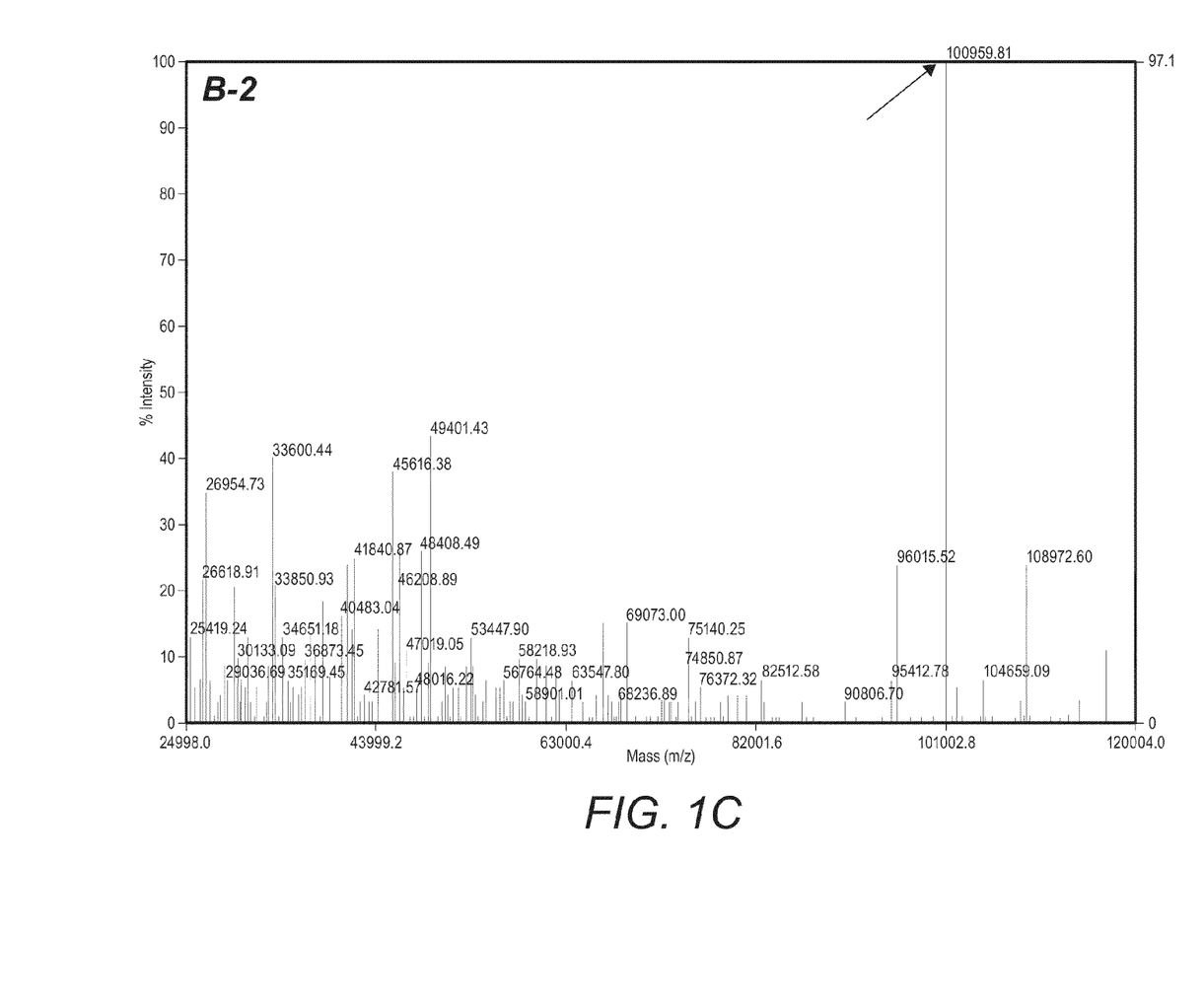
FIG. 1c is a MALDI-TOF spectrum of esterified atelocollagen (B-2).

FIG. 1 contains FT-IR and MALDI-TOF spectra of atelocollagen and esterified atelocollagen, showing the difference therebetween. As seen in FIG. 1a, a distinct peak is read at about 1,900~2,400 (indicated by an arrow) while different values (indicated by an arrow) are observed on the main peaks of MALDI-TOF of FIG. 1b, thus indicating that the collagen was esterified.

EXAMPLE 2

Measurement of Time Taken for Atelocollagen, Succinylated Atelocollagen and Esterified Atelocollagen to Induce Blood Clots 1. Atelocollagen was added in an amount of 2 wt % to PBS and stirred at 4° C. for 24~48 hours.
2. The resulting solution was adjusted to a pH of 7.4 with 0.1M $Na_2HPO_4$.
3. Separately, succinylated atelocollagen was added in an amount of 2 wt % to PBS at 4° C. for 24~48 hours.
4. The resulting solution was adjusted into a pH of 7.4 with 0.1M $Na_2HPO_4$.
5. Blood was sampled from the ear of a rabbit or the abdominal vein of a rat and placed in an amount of 2 mL on each Petri-dish.
6. 1 mL of each of the solutions obtained above and from Example 1 was respectively mixed with the blood samples.
7. The time taken to induce blood clots was measured.

The esterified atelocollagen was found to require two or three minutes for blood coagulation, which is shorter than the four or five minutes taken for coagulation by atelocollagen. On the other hand, no blood clots were found from the blood sample to which succinylated atelocollagen was added.

Figure 2:
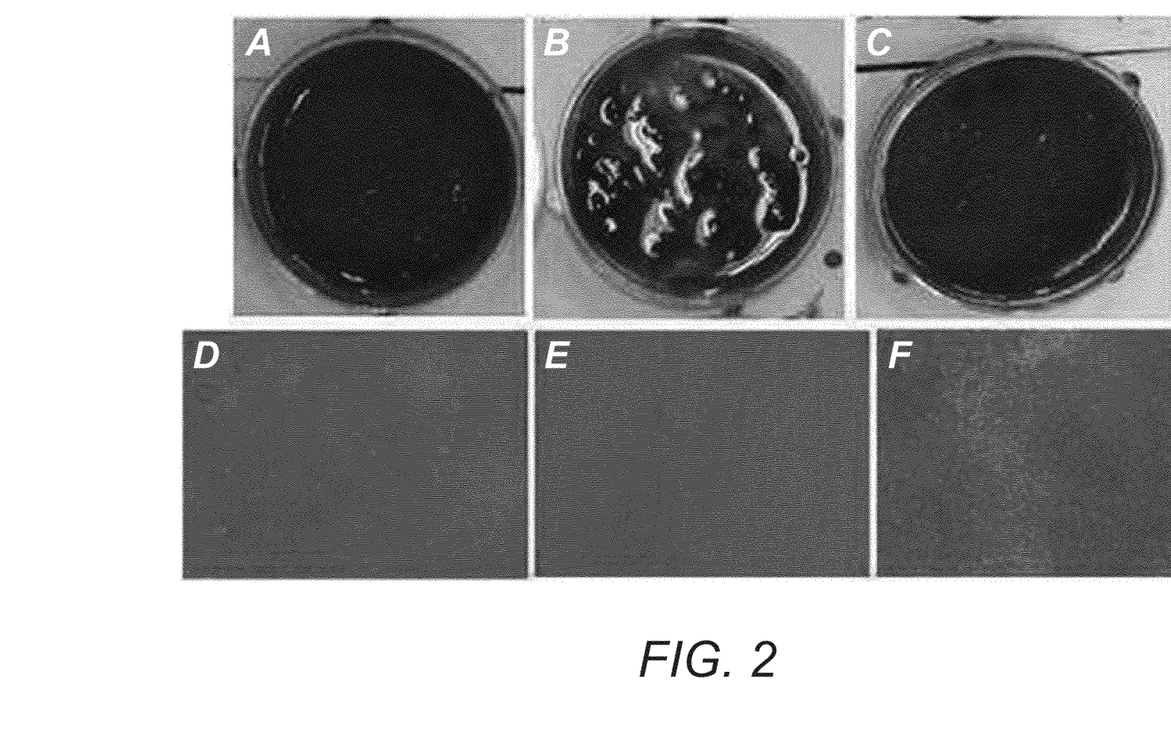
FIG. 2 shows blood coagulation (upper panel) in photographs (upper panel) and in microphotographs (10.08×) (lower panel) in the presence of atelocollagen (A, D), succinylated atelocollagen (B, E) and esterified atelocollagen (C, F).

FIG. 2 shows blood under the coagulation conditions described above in photographs (upper panel) and microphotographs (lower panel).

EXAMPLE 3

Adhesive Strength Between Esterified Atelocollagen and Dopa

1. DOPA was dissolved in amounts of 0.56 wt %, 1 wt %, 1.5 wt %, and 2 wt %.
2. Distilled water, a 0.9 wt % sodium chloride solution, a 1.5 wt % sodium chloride solution and a 1 wt % calcium chloride solution were prepared.
3. DOPA was added in an amount of 0.62 wt % to the 0.9 wt % sodium chloride solution, followed by stirring.
4. DOPA was added in an amount of 0.67 wt % to the 1.5 wt % sodium chloride solution, followed by stirring.
5. DOPA was added in an amount of 0.71 wt % to the 1 wt % calcium chloride solution, followed by stirring.
6. 1 mL of the esterified atelocollagen was added to each Petri-dish.
7. 1 mL of each of the seven solutions, 0.56 wt %, 1 wt %, 1.5 wt % and 2 wt % DOPA solutions of 1 and solutions of 3, 4 and 5, was mixed with 1 mL of the esterified atelocollagen of 6 and monitored for adhesion.

The highest adhesive strength was observed in the esterified atelocollagen to which 0.71 wt % of DOPA in a 1 wt % calcium chloride solution was added.

Figure 3:
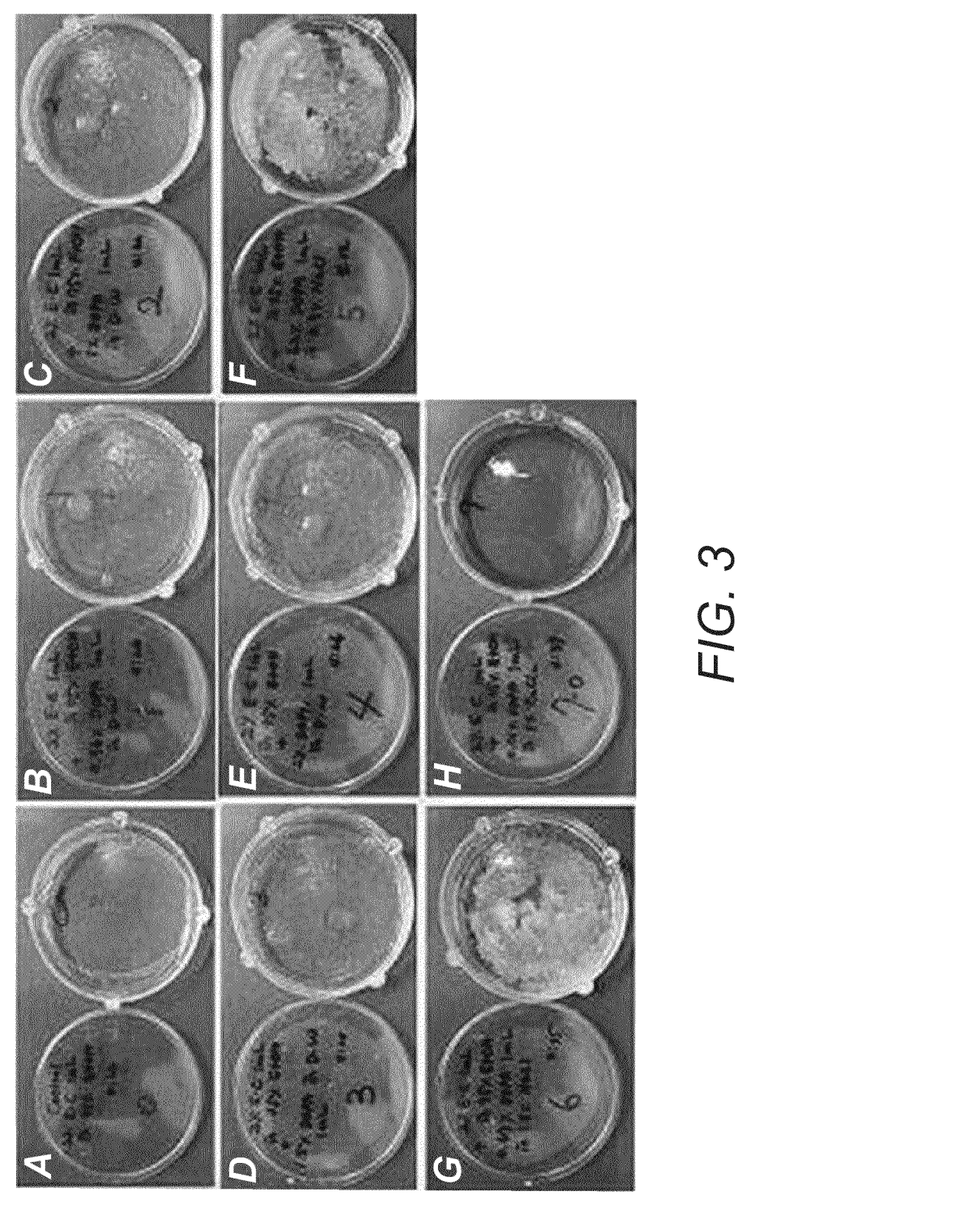
FIG. 3 shows the adhesive states of esterified atelocollagen in the presence or absence of L-DOPA under various conditions: control (esterified atelocollagen) alone (A), esterified atelocollagen+0.56 wt % L-DOPA in D.W (B), esterified atelocollagen+1 wt % L-DOPA in D.W (C), esterified atelocollagen+1.5 wt % L-DOPA in D.W (D), esterified atelocollagen+2 wt % L-DOPA in D.W (E), esterified atelocollagen+0.62 wt % L-DOPA in 0.9 wt % NaCl (F), esterified atelocollagen+0.67 wt % L-DOPA in 1.5 wt % NaCl (G), and esterified atelocollagen+0.71 wt % L-DOPA in 1 wt % $CaCl_2$ (H).
Figure 4:
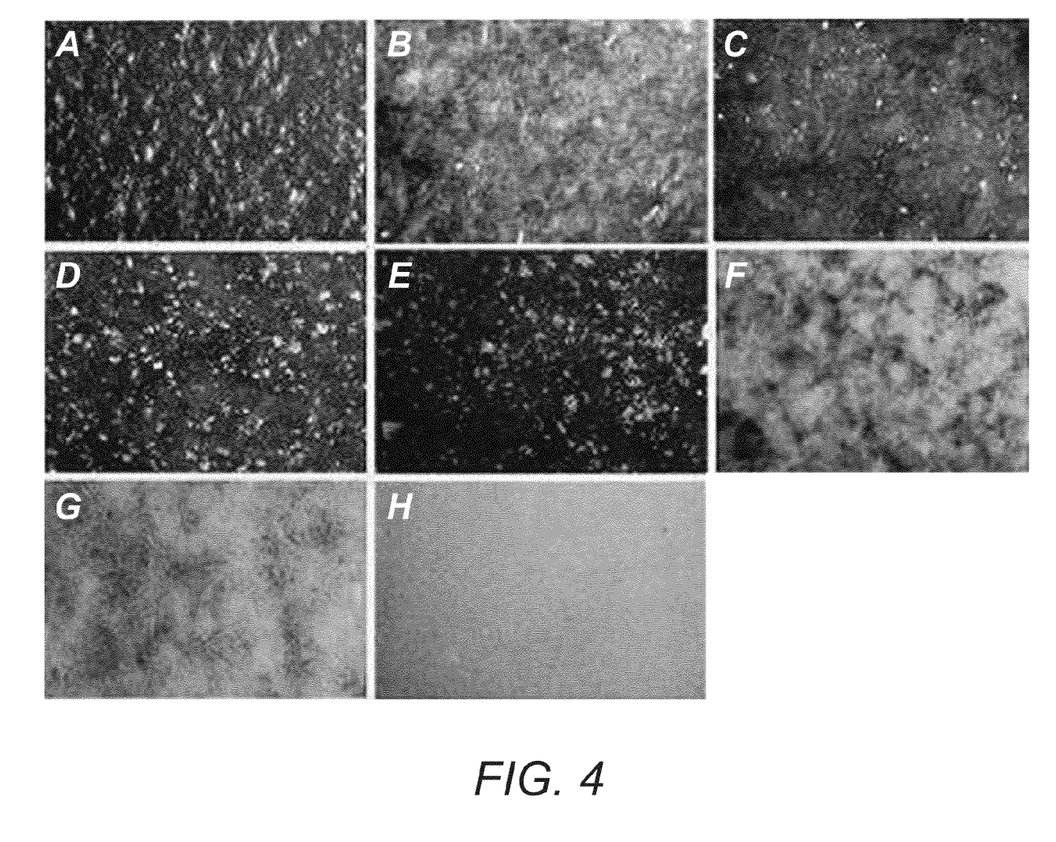
FIG. 4 shows microphotographs of FIG. 3 (10.08 X): control (esterified atelocollagen) alone (A), esterified atelocollagen+0.56 wt % L-DOPA in D.W (B), esterified atelocollagen+1 wt % L-DOPA in D.W (C), esterified atelocollagen+1.5 wt % L-DOPA in D.W (D), esterified atelocollagen+2 wt % L-DOPA in D.W (E), esterified atelocollagen+0.62 wt % L-DOPA in 0.9 wt % NaCl (F), esterified atelocollagen+0.67 wt % L-DOPA in 1.5 wt % NaCl (G), and esterified atelocollagen+0.71 wt % L-DOPA in 1 wt % $CaCl_2$ (H).

FIGS. 3 and 4 show adhesion between esterified atelocollagen and DOPA dissolved in various salt solutions.

EXAMPLE 4

Adhesion of Blood, Esterified Atelocollagen and DOPA

1. DOPA was added in an amount of 0.56 wt % to distilled water, in an amount of 0.67 wt % to a 1.5 wt % sodium chloride solution and 0.71 wt % to a 1 wt % calcium chloride solution, followed by stirring.
2. Blood samples taken from the ear of a rabbit or the abdominal vein of a rat were placed in an amount of 1 mL on respective Petri-dishes.
3. 0.5 mL of the solution of Example 1 and 0.5 mL of each of the three solutions of 1 were added to the Petri-dishes of 2, followed by monitoring for blood clotting and adhesion.

The esterified atelocollagen in admixture with 0.71 wt % of DOPA in 1 wt % calcium chloride solution was found to induce the fastest blood clotting and adhesion.

Figure 5:
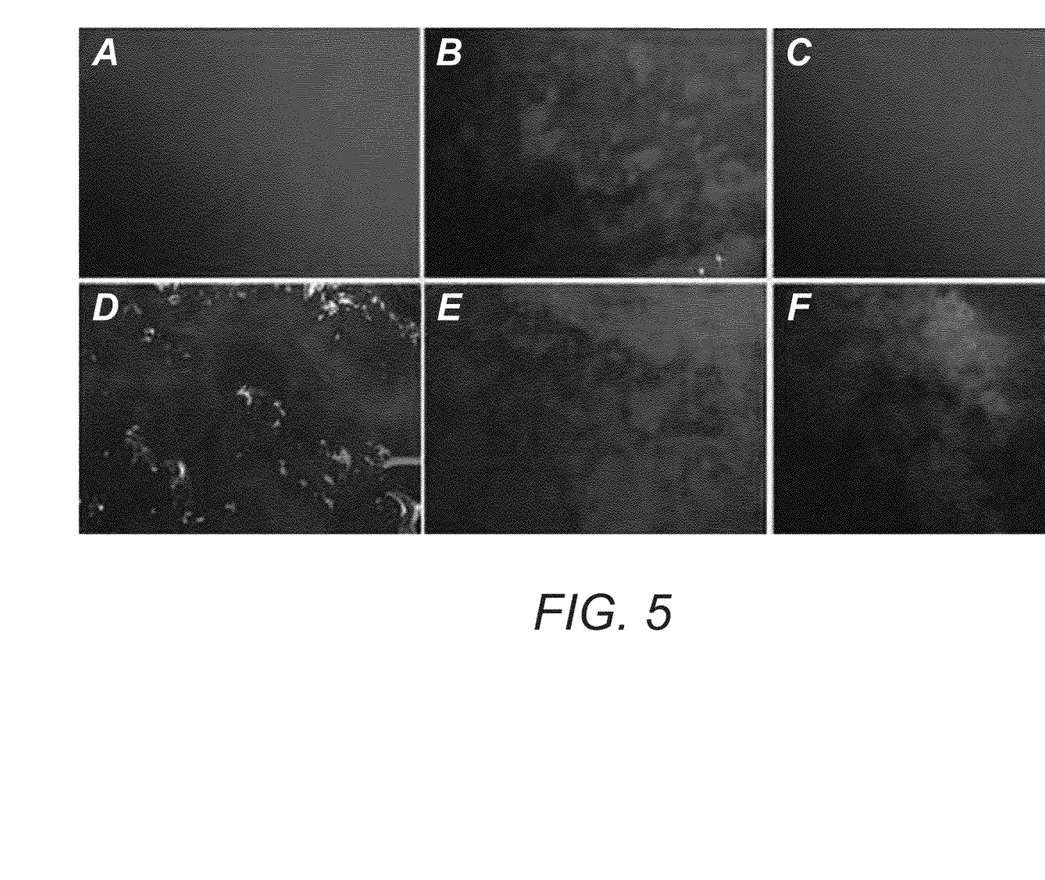
FIG. 5 shows microphotographs of the blood subjected to coagulation under various conditions: Control 1 (blood alone, A), Control 2 (blood+collagen, B), Control 3 (blood+Ca(Na)$Cl_2$, C), blood+esterified atelocollagen+0.56 wt % L-DOPA in D.W (D), blood+esterified atelocollagen+0.67 wt % L-DOPA in 1.5 wt % NaCl (E), and blood+esterified atelocollagen+0.71 wt % L-DOPA in 1% $CaCl_2$ (F).

FIG. 5 shows microphotographs of the blood subjected to coagulation under various conditions.

EXAMPLE 5

Effect of Tranexamic Acid on Blood Coagulation

While tranexamic acid, a hemostatic agent with antifibrinolytic activity, was used under the above-described conditions, the time taken to induce blood clots was monitored.
—Experimental Condition A
1. 0.5 mL of blood was placed on each Petri-dish.
2. A mixture of 0.25 mL of the solution of Example 1 and 0.25 mL of the 1 wt % calcium chloride solution containing 0.71 wt % of DOPA and 0.02 wt % of tranexamic acid was added to the Petri-dish of 1.
3. A mixture of 0.25 mL of the solution of Example 1 and 0.25 mL of the 1 wt % calcium chloride solution containing 0.71 wt % of DOPA and 0.05 wt % of tranexamic acid was added to the Petri-dish of 1.
4. A mixture of 0.25 mL of the solution of Example 1 and 0.25 mL of the 1 wt % calcium chloride solution containing 0.71 wt % of DOPA and 0.1 wt % of tranexamic acid was added to the Petri-dish of 1.
5. Reactions in the Petri-dishes were observed.

All of the mixtures were observed to induce blood coagulation immediately after the addition thereof and form apparent blood clots 1~2 min after the addition. The blood was completely coagulated to form clots in all of the petri-dishes.
—Experimental Condition B
1. 0.5 mL of blood was placed on each Petri-dish.
2. A mixture of 0.25 mL of the solution of Example 1 and 0.25 mL of the 1.5 wt % calcium chloride solution containing 0.67 wt % of DOPA and 0.02 wt % of tranexamic acid was added to the Petri-dish of 1.
3. A mixture of 0.25 mL of the solution of Example 1 and 0.25 mL of the 1.5 wt % calcium chloride solution containing 0.67 wt % of DOPA and 0.05 wt % of tranexamic acid was added to the Petri-dish of 1.
4. A mixture of 0.25 mL of the solution of Example 1 and 0.25 mL of the 1.5 wt % calcium chloride solution containing 0.67 wt % of DOPA and 0.1 wt % of tranexamic acid was added to the Petri-dish of 1.
5. Reactions in the Petri-dishes were observed.

As soon as they were added, all of the mixtures induced blood coagulation, but it took as long as about 10 min to form blood clots, which was quite different from the time it took in Experimental Condition A.
—Experimental Condition C
1. 0.5 mL of blood was placed on each Petri-dish.
2. A mixture of 0.25 mL of the solution of Example 1 and 0.25 mL of distilled water containing 0.56 wt % of DOPA and 0.02 wt % of tranexamic acid was added to the Petri-dish of 1.
3. A mixture of 0.25 mL of the solution of Example 1 and 0.25 mL of distilled water containing 0.56 wt % of DOPA and 0.05 wt % of tranexamic acid was added to the Petri-dish of 1.
4. A mixture of 0.25 mL of the solution of Example 1 and 0.25 mL of distilled water containing 0.56 wt % of DOPA and 0.1 wt % of tranexamic acid was added to the Petri-dish of 1.
5. Reactions in the Petri-dishes were observed.

Blood coagulation was induced just after the addition of each of the mixtures, but it took a longer time than it did in Experimental Condition A to form apparent blood clots.
—Experimental Condition D
1. 0.5 mL of blood was placed on each Petri-dish.
2. A mixture of 0.25 mL of the solution of Example 1 and 0.25 mL of 1 wt % calcium chloride solution containing 0.71 wt % of DOPA was added to the Petri-dish of 1.
3. A mixture of 0.25 mL of the solution of Example 1 and 0.25 mL of 1.5 wt % calcium chloride solution containing 0.67 wt % of DOPA was added to the Petri-dish of 1.
4. A mixture of 0.25 mL of the solution of Example 1 and 0.25 mL of distilled water containing 0.56 wt % of DOPA was added to the Petri-dish of 1.
5. Reactions in the Petri-dishes were observed.

A longer time for blood coagulation to form clots was measured compared to when in the presence of tranexaminic acid.
—Experimental Condition E
1. 0.5 mL of blood was placed on each Petri-dish.
2. 0.25 mL of the solution of Example 1 was added to the Petri-dish of 1.
3. Reactions in the Petri-dishes were observed.

The blood was observed to coagulate in the presence of the esterified atelocollagen, unlike blood without any additives, but at a slower rate than when in the presence of tranexamic acid.
—Experimental Condition F
1. 0.5 mL of blood was placed on each Petri-dish.
2. 0.25 mL of a 0.02 wt % tranexamic acid solution in distilled water was added to the Petri-dish of 1.
3. 0.25 mL of a 0.05 wt % tranexamic acid solution in distilled water was added to the Petri-dish of 1.
4. 0.25 mL of a 0.1 wt % tranexamic acid solution in distilled water was added to the Petri-dish of 1.
5. Reactions in the Petri-dishes were observed.

Unlike blood without any additives, the blood was observed to coagulate in the presence of tranexamic acid, but at lower rates than when in the presence of the esterified atelocollagen.

As described above, because of being based on non-blood constituents, the adhesive hemostatic agent of the present invention has no possibility of mediating particular diseases or viral infections (HIV, HCV, HBV, CMV, etc), unlike conventional agents comprising blood constituents. The adhesive hemostatic agent of the present invention comprises porcine esterified atelocollagen, which is free of TSE's (Transmissible Spongiform Encephalopathies), and anaphylaxis unlike bovine proteins, causes no immune responses and can become positively charged thereon allowing for quick binding to negatively charged platelets, L-DOPA (3,4-dihydroxyphenyl alanine) which functions to stabilize collagen fibers, thus increasing the adhesive activity of the adhesive hemostatic agent, and a salt which serves to promote coagulation. Further, an antifibrinolytic, when used in combination with the esterified atelocollagen, provides the long-term stabilization, high adhesive strength and excellent tissue sealing activity to the adhesive hemostatic agent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

I claim:

1. A method for preparing a collagen-based adhesive hemostatic agent, comprising:
   (a) removing immunogenic telo-peptides from porcine collagen through enzyme treatment to afford an atelocollagen;
   (b) reacting an aqueous solution of the atelocollagen with an ethanol solution to afford an esterified atelocollagen;
   (c) adding 3,4-dihydroxy-phenyl alanine to an aqueous solution containing calcium chloride;
   (d) mixing an aqueous solution containing the esterified atelocollagen with the aqueous solution obtained by the step (c); and
   wherein the 3,4-dihydroxy-phenyl alanine is oxidized into catecholamine which is associated with a lysine moiety of the esterified atelocollagen, so as to provide adhesiveness to the hemostatic agent.

2. The method as defined in claim 1, wherein an antifibrinolytic is further added to the aqueous solution obtained by the step (c).

3. The method as defined in claim 2, wherein the antifibrinolytic is tranexamic acid or aminocaproic acid.

* * * * *